United States Patent [19]

Knight et al.

[11] Patent Number: 5,049,388

[45] Date of Patent: Sep. 17, 1991

[54] SMALL PARTICLE AEROSOL LIPOSOME AND LIPOSOME-DRUG COMBINATIONS FOR MEDICAL USE

[75] Inventors: Jack V. Knight; Brian E. Gilbert; Samuel Z. Wilson, all of Houston, Tex.; Howard R. Six, East Stroudsborg, Pa.; Philip R. Wyde, Houston, Tex.

[73] Assignee: Research Development Foundation, Carson City, Nev.

[21] Appl. No.: 383,383

[22] Filed: Jul. 21, 1989

Related U.S. Application Data

[63] Continuation-in-part of Ser. No. 927,898, Nov. 6, 1986, abandoned, and a continuation-in-part of Ser. No. 239,512, Sep. 1, 1988, abandoned.

[51] Int. Cl.$^5$ ............................................. A61K 37/22
[52] U.S. Cl. ..................................... 424/450; 424/43; 428/402.2; 264/4; 264/4.1
[58] Field of Search ......................... 252/305; 264/413; 428/402.2; 424/43, 417, 450; 436/829, 826; 514/885, 958

[56] References Cited

U.S. PATENT DOCUMENTS 4,438,052  3/1984  Weder et al. ..................... 264/4.6

FOREIGN PATENT DOCUMENTS 0084898  8/1983  European Pat. Off. ............ 424/450
8601714  3/1986  PCT Int'l Appl. ................. 424/450

OTHER PUBLICATIONS

Chemical Abstracts, 103:27287f (1985), McGurk et al.
Chemical Abstracts, 105:197191d (1986), McGurk.

Primary Examiner—Thurman K. Page
Assistant Examiner—Donald R. McPhail
Attorney, Agent, or Firm—James F. Weiler

[57] ABSTRACT

Disclosed are aqueous aerosol droplets containing liposome or interacted liposome-drug or medication combination particles in a continuous phase of air or oxygen-enriched air advantageous for the treatment of a wide variety of diseases. The drug or medication is interacted with the liposome membrane so that on its rupture the drug or medication is not lost from the liposome. Different methods of preparation of the aerosol particles containing the liposome and interacted liposome-drug combination particles are described which can be used in small particle aerosol treatment. The majority of the aerosol droplets containing the liposome particles alone or with drugs has a diameter less than 5 microns and has an aerodynamic mass median diameter ranging from about 1 to 3 microns, and the liposome and interacted-liposome drug particles are substantially uniform in size and less than 1 micron in diameter.

25 Claims, 7 Drawing Sheets

SMALL PARTICLE AEROSOL LIPOSOME AND LIPOSOME-DRUG COMBINATIONS FOR MEDICAL USE

RELATED APPLICATION

The present application is a continuation-in-part of U.S. application Ser. No. 927,898, filed Nov. 6, 1986, abandoned in favor of U.S. application Ser. No. 239,512 filed Sept. 1, 1988, abandoned in favor of this application.

FIELD OF THE INVENTION

The field of the invention is small particle aerosol liposomes and liposome-drug combinations advantageous for medical use.

BACKGROUND OF THE INVENTION

Small particle aerosol is defined as a colloid system in which the continuous phase is a gas, and the majority of particles are less than 5 microns in diameter with an aerodynamic mass median diameter ranging from 1 to 3 microns. The advantage of such a discretely sized population of particles is that, because of their small size and low settling velocities, they will penetrate when inhaled into the lower respiratory tract in substantial percentages. For example, 1.5 micron particles will deposit 46 percent of the total inhaled dose in the lung and another 36 percent in nose and upper air passages. Such uniform deposition will permit treatment of lesions at any level of the respiratory tract (Gilbert, B. E., Wilson, S. Z., and Knight, V., 1986, Ribavirin Aerosol Treatment of Influenza Virus Infections. In: Options for the Control of Influenza. UCLA Symposium on Molecular and Cellular Biology. Alan R. Liss, Inc., New York, N.Y., p. 343.)

Small particle aerosol treatment delivers a high dose of drug to the epithelium of the respiratory tract in amounts largely unachievable by other routes of administration (Knight, V. 1973, Airborne Transmission and Pulmonary Deposition of Respiratory Viruses. In: Viral and Mycoplasmal Infections of the Respiratory Tract. V. Knight, ed. Lea and Febiger, Philadelphia, Pa., p. 1). There is a subsequent steady rate of absorption of drug into the systemic circulation.

Dried phospholipids placed into an aqueous environment will spontaneously associate into multilamellar structures that function as permeability barriers. These lipid vesicles, termed liposomes, are composed of aqueous compartments separated from each other and the external medium by a series of closed concentric lipid bilayers. The composition of the aqueous compartments is the same as the medium in which the liposomes were formed; this makes it possible to entrap a wide variety of materials within the lipid bilayers. Entrapped markers can be released by a variety of lytic agents in a manner analogous to natural membranes. Since liposomes may be prepared from substances found in normal cell membranes, they are perceived as nontoxic to mammalian host; and studies in humans and laboratory animals have supported this concept.

The ability to encapsulate water soluble compounds in liposomes led to speculation that they might be useful clinically as carriers of drugs. This expectation has not been fully realized for water soluble drugs. However, recent studies with water insoluble anticancer and antimicrobial compounds have suggested that liposomes may be ideally suited for delivery of this type of drug. The amounts of drug associated with liposomes are high and release does not occur until the membranes are destroyed either by mechanical means of biodegradation, thus allowing a more controlled release of the drug over time. Moreover, in laboratory animals the use of liposomes actually reduced toxic effects observed with the drug alone.

Liposome-drug compounds are heterogeneous in size ranging from less than 1 micron up to 10 microns in diameter and have been given in relatively large oral or intravenous doses.

DESCRIPTION OF THE PRIOR ART

Applicants are unaware of any prior art disclosing, suggesting, or teaching small particle aqueous aerosol droplets containing liposomes and liposome-drug particles propelled by air or oxygen-enriched air for medical use or that the heterogeneous size of small liposomes and liposome-drug particles can be reduced to a more homogeneous population of small liposome and liposome drug particles (<1 micron in diameter) without leakage of the drug upon destruction of the liposome membranes. The size of the aerosol particle is controlled by the operating characteristics of the aerosol generator or nebulizer without any loss in effectiveness thereof.

Liposomes are effective carriers for the introduction of various agents into cells in in vitro experiments. A large number of scientific papers have been published describing liposomes as carriers for both water-soluble and lipid soluble agents. Several hundred different substances have been entrapped in liposomes. For a further description of liposomes, their preparation and application, reference is made to American Laboratory, pages 125–135 Oct., 1985.

The following articles and patents are representative of the prior art:

*AMA Drug Evaluation*, 5th Edition, pp. 1162–1166

*Annals NYAS*, "Liposomes in Therapeutic and Preventive Medicine: The Development of the Drug-Carrier Concept", G. Gregoriadis, 1978, 308:343–65

*Clinical Science and Mol. Med.*, "Tissue and Hepatic Subcellular Distribution of Liposomes Containing Bleomycin after Intravenous Administration to Patients with Neoplasms", A. W. Segal, G. Gregoriadis, J. P. Lavender, D. Tarin, T. J. Peters, 1976, 51:421–25

*J. Infect. Dis.*, "Liposomal Amphotericin B for the Treatment of Systemic Fungal Infections in Patients with Cancer: A Preliminary Study", G. Lopez-Berenstein, V. Fainstein, R. Hopfer, K. Mehta M. Sullivan, M. Keating, M. Rosenblum, R. Mehta, M. Luna, E. Hersh, J. Reuben, R. Juliano, G. Bodey, 1985, 151:704–10

*Infect. Immun.*, "Effect of Liposomal Amphotericin B on Murine Macrophages and Lymphocytes", R. Mehta, K. Mehta, G. Lopez-Berenstein, R. Juliano, 1985, 47:429–33

*The Lancet*, "Artificial Surfactant Therapy in Hyaline-Membrane Disease", T. Fujiawara, H. Maeta, S. Chida, T. Morita, Y. Watabe, T. Abe, 1980, 1:55–59

*Pediatrics*, "Hyaline Membrane Disease Treated with Bovine Surfactant", J. A. Smyth, I. L. Metcalfe, P. Duffty, F. Possmayer, M. H. Bryan, G. Enhorning, 1983, 71:913–17

*Pediatrics*, "Isolation of Human Surfactant from Amniotic Fluid and a Pilot Study of its Efficacy in Respiratory Distress Syndrome", M. Hallman, T. A. Merritt, H. Schneider, B. Epstein, F. Mannino, D. Edwards, L. Gluck, 1983, 71:473-82

*Pediatric Res.*, "Nebulization of Sonicated Phospholipids for Treatment of Respiratory Distress Syndrome of Infancy", H. H. Ivey, J. Kattinwinkel, S. Roth, 1977, 11:301-14

*The Lancet*, "Dry Artificial Lung Surfactant and its Effect on Very Premature Babies", C. J. Morley, A. D. Banham, N. Miller, J. A. Davis, 1981 1:64-68

*The Lancet*, "Controlled Trial of Artificial Surfactant to Prevent Respiratory Distress Syndrome", H. L. Halliday, G. McClure, M. Reid, T. R. J. Lappin, C. Meban, P. S. Thomas, 1984, 1:476-78

U.S. Pat. No. 4,370,349 disclosing a process for preparing a freeze-dried potential liposome mixture U.S. Pat. No. 3,873,720 disclosing an aqueous mixture of fat, carbohydrate and amino acids emulsified with the aid of long chain fatty acid or its basic amino acid salts and egg-yolk phospholipids.

U.S. Pat. No. 4,073,943 disclosing parenteral administration of water-insoluble pharmacologically active agents in lipoyd phase.

U.S. Pat. No. 4,168,308 disclosing parenteral administration of water-insoluble pharmacologically active agents in lipoyd phase.

U.S. Pat. No. 4,536,519 directed to an emulsifying agent and emulsified cosmetics.

U.S Pat. No. 4,563,354 disclosing parenteral administration of oil and water emulsions.

*Chemical Abstracts*, 105:197191d (1986) discloses aerosol pharmaceuticals containing liposomes of 30-1000 mm diameter in a gas fluorocarbon. No mention is made of the aerosol particle size.

European Patent Application 0084898, 8/3/83, makes general references to nebulized aqueous suspensions without any indication as to the size of the aerosol particles.

*Chemical Abstracts* 103:27287f (1985) and International Application Publication No. W086/01714 (1986) disclose aerosol-liposome compositions.

SUMMARY OF THE INVENTION

The present invention is directed to small particle aqueous aerosol droplets containing liposomes and interacted drug-liposome combinations propelled in air or oxygen-enriched air having advantageous properties for medical use. Small particle aerosol, as used herein, is a colloid system in which the continuous phase is air or oxygen-enriched air, and the majority of aerosol particles is less than 5 microns in diameter with an aerodynamic mass median diameter ranging from 1 to 3 microns. Before aerosolization the liposomes are heterogeneous in size ranging from less than 1 micron up to 10 microns in diameter. Advantageously, the partiole size of the liposomes and the liposome-drug particles are substantially homoqenized by the aerosol nebulizer to sizes of less than one micron in diameter. Most particles are much less than 1 $\mu$m in diameter and several may be included in the aqueous particles generated by the aerosol generator. These smaller liposome and liposome-drug particles retain their pharmacological activity.

Small particle aerosol treatment containing liposomes alone is advantageous since liposomes can closely mimic pulmonary surfactant and may repair defects in this system that have developed for a variety of reasons.

Aerodynamic mass median diameter is the size of a population of particles measured by their inertial parameter (rate at which they settle in still air) and assuming a spherical particle of unit density. This is sometimes termed "Stokes Diameter" or equivalent mean diameter (An Introduction to Experimental Aerobiology, Robert L. Dimmick, Ann B. Alsers, Wiley Interscience, p. 447; Aerosol Science, C. N. Davies, Academic Press, 1966, p. 306).

Small particle aerosol treatment with interacted drug liposome particles is advantageous in that, when the liposome permeability barrier is damaged, such as during aerosolization, the drug is not prematurely released from the liposome.

The drugs to be given by liposome-drug combinations range widely as does the dosage. In general, the drugs in recommended dosages for non-aerosol liposome-drug combinations of the prior art can be used for the small particle aerosol liposome-drug combinations without the disadvantages of the prior art liposome-drug combinations. The amount of the drug in the liposome-drug combination aerosol is controlled by the concentration of drug in the reservoir of the aerosol generator. Also, the amount of drug employed depends on the duration of treatment, drug used and the like. For example, dosage for 24 hours can range from less than a nanogram to a few grams depending on need, toxicity, biological and chemical properties of the drug, and other factors. Liposome-drug or medication combinations include those which interact with the liposome membrane so that on rupture of the membrane the drug or medication is not lost from the liposome, referred to herein as lipophilic drugs or medications interacted with the liposome membrane.

Preferably, the liposomes are multilamellar although unilamellar liposomes can be used and interacted with the drug or medication.

Accordingly, it is an object of the present invention to provide small particle aqueous aerosol containing liposomes or liposome-drug particles propelled or carried by air or oxygen- C enriched air for medical use.

A further object of the present invention is the provision of a method of processing liposomes by an aerosol nebulizer propelled by air or oxygen-enriched air from heterogeneous sizes to substantially uniform small particle liposomes (<1 micron in diameter) without loss of effectiveness while carried in small particle aqueous droplets.

A still further object of the present invention is the provision of a method of processing interacted drug liposome combination particles by an aerosol nebulizer from heterogeneous sizes to substantially uniform, small particles of liposome-drug combinations carried in small particle aqueous droplets without premature release of the drug from the liposomes and, hence, any loss of effectiveness.

A further object of the present invention is the provision of treating a patient with liposomes by delivering with air or oxygen-enriched air small aqueous particles containing liposomes to the epithelium of the respiratory tract.

A still further object of the present invention is the provision of treating a patient by delivering with air or oxygen-enriched air small aerosol particles containing interacted drug liposome particles to the epithelium of the respiratory tract.

A further object of the present invention is the provision of such small particle aqueous aerosols containing particles of liposome-drug combinations in which a wide variety of drug combinations for a wide variety of disease can be administered safely and effectively to the patient.

Other and further objects, features, and advantages of the present invention appear throughout and are inherent therein.

DESCRIPTION OF PRESENTLY PREFERRED EMBODIMENTS

Figure 1:
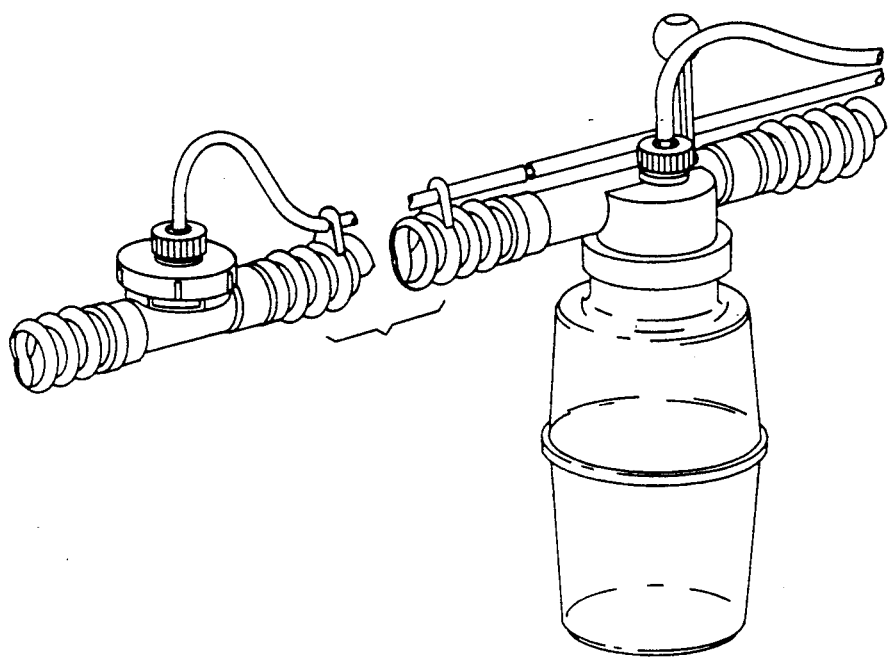
FIGS. 1 and 1A are views of two commercially available nebulizers, the Puritan Bennett nebulizer, FIG. 1 being model No. 1920, and FIG. 1A being model No. 1917, useful in generating aqueous small particle aerosol droplets containing liposomes and liposome-drug particles in air or oxygen-enriched air of the invention.

As previously set forth, the present invention is directed to small particle aqueous aerosol particles containing liposomes and interacted drug liposome combination particles propelled or carried in air or oxygen-enriched air to methods of generating aerosols of them, and to methods of treating patients with them. As the term "Small particle aerosol" is used herein, it is defined as a colloid system in which the continuous phase is an air or oxygen-enriched air, and the majority of the aerosol particles or droplets is less than 5 microns in diameter with an aerodynamic mass median diameter ranging from 1 to 3 microns and containing liposomes or liposome drug particles less than 1 micron in diameter. Liposome-drug combinations of the prior art are heterogeneous in size ranging from less than 1 micron up to 10 microns in diameter and have been given to patients in relatively large oral or intravenous doses. Such dosage may result in high plasma concentrations but low concentrations in the respiratory epithelium. Unexpectedly, the heterogeneous liposome particles and the interacted drug liposome combination particles can readily be converted to a more homogeneous small size by an aerosol nebulizer without any loss in effectiveness of the liposomes and interacted drug liposome combination particles while contained in aqueous aerosol particles of the above diameter size while propelled or carried in air or oxygen-enriched air. Advantageously, these small particle aqueous aerosol droplets containing these liposomes and liposome-drug combinations, when inhaled, provide high concentration on the respiratory epithelium and a steady rate of absorption into the circulation without the hazard of peak levels that may be associated with large oral or intravenous doses of drug, and deliver a high dose of drug to the epithelium of the respiratory tract in amounts largely unachievable by other routes of administration. One to several liposomes or liposome-drug particles (<1 micron in diameter) may be contained in a single aerosol droplet (1-3 micron, aerodynamic mass median diameter) depending on the concentration of liposome material in the preparation that is to be nebulized. As previously mentioned, the advantage of such a discretely sized population of particles is that because of their small size and low settling velocities they will penetrate when inhaled into the lower respiratory tract in substantial percentages. For example, 1.5 micron particles will deposit 46% of the total inhaled in the lung and another 36% in the nose and upper air passages. Such uniform deposition permits treatment of lesions at any level of the respiratory tract and also provides an interface into the cell without the problems and disadvantages associated with oral and intravenous injections.

Interaction of the drug or compound with liposomes can be done in one or more of a number of ways such as 1) intercalated into the lipid bilayer, 2) covalently attached to a lipophilic compound (e.g., phospholipid) which is inserted into the lipid bilayer, 3) trapped between the phospholipid layers which comprise the lipid bilayer, or 4) a component soluble in the aqueous phase, but whose chemical properties (e.g., hydrophobic ionic, or Van der Waals forces) allow an interaction with the phospholipid bilayer such that when the liposome permeability barrier is damaged, the compound is not released from the liposome.

The following Table 1 describes medications of lipophilic nature which may be interacted with the lipid of liposome and be administered by small particle aerosol.

TABLE 1

Doses of drugs that interact with liposomes and may be administered in a liposome formulation by small particle aerosol inhalation. Average adult doses for some indications are given:

| Cardiac glycosides | |
|---|---|
| Digitoxin | 1.2 to 1.6 mg, loading dose, 0.1 mg daily, maintenance dose |
| Digoxin | 8-12 microgram/kg, loading dose, 2.5-4 microgram/kg, maintenance dose |
| Anti-convulsant | |
| Tegritol | 600-800 mg/day |
| Anti-parasitic | |
| Praziquantel | 25-60 mg/kg/day for 1-2 days |
| Anti-arrhythrmic | |
| Isosorbide | 2.5-10 mg/dose, repeat according to response |
| Hormones | |
| Anti-diuretic (ADH) (Vasopressin) | 5 to 60 units/day |
| Cortico steroids Daily Doses | |
| Drug | Equivalent Dose/Day |
| Cortisone | 25 mg-50 mg |
| Hydrocortisone | 20 mg-40 mg |
| Prednisolone | 5 mg-10 mg |
| Meprednisone | 4 mg-8 mg |

TABLE 1-continued

Doses of drugs that interact with liposomes and may be administered in a liposome formulation by small particle aerosol inhalation. Average adult doses for some indications are given:

| | |
|---|---|
| Methylprednisolone | 4 mg-8 mg |
| Triamcinolone | 4 mg-8 mg |
| Paramethasone Acetate | 2 mg-4 mg |
| Dexamethasone | 0.750 mg-1.5 mg |
| Betamathasone | 0.6 mg-1.2 mg |
| Testosterone | 10-25 mg, 3 times/week |
| Estrogen, Natural | 1-2 mg/day |
| Thyroxine | 1-2 mg/day |
| Androgens | 200-400 mg/day |
| Hydroxy progesterone | 375 mg every 4 weeks |
| Anti-diabetic | |
| Acetohexamide | 0.5-1 gm/day |
| Chlorpropamide | 100-250 mg/day |
| Tolbutamide | 100-250 mg-3.0 gm/day |
| Anti-hormone | |
| Bromocriptine mesylate | 1.25-2.5 mg/day |
| Immune suppressive | |
| Cyclosporine A | 500 mg-1000 mg/day |
| Anticancer | |
| Uracil mustard | 0.10-0.15 mg/kg weekly for 4 weeks |
| Methotrexate | |
| Anti-fungal | |
| Amphotericin B | 50-100 mg/day |
| Ketoconazole | 100-200 mg/day |
| Griseofulvin | 330-375 mg/day |
| Miconazole | 100-200 mg/day |
| Tranquilizers | |
| Chlorpromazine | 30-75 mg/day |
| Fluphenazine decanoate | 5-10 mg/day |
| Reserpine | 0.25 mg/day |
| Antihistamines | |
| Terfenadine | 40-600 mg/day |
| Anti-viral | |
| Acyclovir | 800-1000 mg/day |
| Azidothymidine | 800-1000 mg/day |
| Ganciclovir | 800-1000 mg/day |
| Enviroxime | 10-20 mg/day |
| Winthrop 51711 | 20-40 mg/day |
| Anti-malarial | |
| Chloroquine phosphate | 300 mg/week |
| Vaccines (purified sub-units) | |
| Human Immunodeficiency virus | |
| Influenza virus | 5-20 micrograms/dose |
| Respiratory syncytial virus | |

The following Table 2 shows drugs that are water solbule but which, if derivatized to be lipophyllic, can be prepared as drugs in Table 1 and be administered as liposome aerosol.

TABLE 2

Substances which are substantially water soluble that if suitably derivatized so that they interact with lipid of liposomes can be administered in small particle aerosol

| Antiasthma | Antiarrhythimic | Tranquilizers |
|---|---|---|
| metaproterenol | propanolol | hydroxyzines |
| aminophylline | atenolol | |
| theophylline | verapamil | Antihistamines |
| terbutaline | captopril | pyribenzamine |
| ephedrine | | chlorpheniramine |
| isoproterenol | Hormones | diphenhydramine |
| adrenalin | ACTH | |
| norepinephrine | gonadotropin | |
| Antihypertensives | Antidiabetic | Sedatives & Analgesic |
| apresoline | insulin | dilaudid |
| atenolol | | demerol |
| | | oxymorphone |
| Antiparasitic | | |
| pentamidine | Anticancer | Vaccines |
| | azathioprine | Hemophilus influenza |
| Antibiotic | bleomycin | Pneumococcus |
| penicillin | adriamycin | |
| tetracycline | daunorubicin | Antifungal |
| cephalothin | vincristine | miconazole |
| cefotaxime | | |
| carbenicillin | Immunotherapies | Antiviral |
| vancomycin | interferon | ribavirin |
| gentamycin | interleukin-2 | rimantadine/ |
| tobramycin | monoclonal antibodies | amantadine |
| piperacillin | gammaglobulin | |
| moxalactam | | Other |
| cefazolin | Antihypotension | cell surface receptor |
| cefadroxil | dopamine | blocking agents |
| cefoxitin | dextroamphetamine | |

Liposome Preparation

The liposomes preferably are multilamellar, although unilamellar liposomes may be used, and the liposomes and intereacted liposome-drug combinations may be prepared in any suitable manner, for example, as described in American Laboratory, pp. 125-135, Oct., 1985, and U.S. Pat. No. 4,370,349; Evans, et. al., Jan. 25, 1983. These publications amply document that a variety of amphipathic lipids are suitable for preparing of liposomes for use in this invention.

Suitable lipids include the phospholipids, for example the natural lecithins derived from egg-yolk or soyabean, sphingomyelin derived from beef brain or synthetic lecithins, for example dimyristoyl-phosphatidylcholine, dipalmitoylphosphatidylcholine or distearoylphosphatidylcholine, or unsaturated synthetic lecithins, for example, dioleylphosphatidylcholine or dilinoleylphosphatidylcholine. Either a single phospholipid or a mixture of phospholipids may be used. Sterols, for example, cholesterol or ergosterol, may be added to increase stability of the liposomal bilayers and lipids possessing a positive or negative change, for example, phosphatidylethanolamine, beef brain ganglioside or phosphatic acid may be used to render the appropriate charge to the liposome and to increase the size of the aqueous compartments. Mixtures of lipids may be used to render the liposomes more fluid or more rigid and to increase or decrease permeability characteristics.

Liposomes can be prepared by a variety of methods. These procedures have in common the dispersal of a phospholipid or mixture of lipids into a suitable container and the removal of an organic solvent, for example, ether, chloroform, or T-butanol, by methods such as evaporation, rotary evaporation under vacuum or lyophilization with commercially available freeze-drying equipment. Dispersing the resulting lipid film of dry lipid powder in an aqueous medium, for example, distilled water, isotonic saline or buffered solutions will result in the formation of liposomes. For example, phosphatidylcholine is dissolved in re-distilled T-butanol and transferred to a bottle. The solution is frozen and the solvent is removed under vacuum using a commercial freeze-dryer. Sterile pyrogen-free distilled water is added to the freeze dried powder and the bottle shaken to disperse the powder. The resulting milky suspension can be examined microscopically and the suspension shown to contain liposomes that are heterogeneous in size ranging from less than 1 micron up to 10 microns.

Any biologically active compound (medication) may be associated with liposomes. Whether the compound is associated with the lipid portion of the liposomes or resides in the aqueous compartments is dependent upon the physical and chemical properties of the compound of biological interest. It is understood that the procedures used for preparing liposome-drug combinations are not restricted under this invention, any procedure that results in liposomes would be applicable. For purposes of disclosure, two general methods of producing interacted drug liposomes are described below. They illustrate that regardless of chemical and physical properties a wide array of biologically active compounds or medications can be interacted with liposomes and that such liposomes are applicable to delivery by small particle aerosol.

Method I may be used to incorporate lipid soluble or lipid-bound biologically active compounds or medications. For example, egg lecithin (phosphatidylcholine) or similar phospholipids dissolved in an organic solvent is transferred to a suitable flask or bottle. The desired lipid soluble compound is added, the solution is frozen and the solvent is removed using a commercial freeze-dryer. Liposomes are formed by the addition of a suitable aqueous medium, for example, sterile distilled water, isotonic saline or a buffered solution followed by vigorous shaking of the container. It is recognized that the phospholipid or mixture of phospholipid used to prepare the liposomes can be altered to increase or decrease the lipid solubility of the active compound as desired and that solvents such as chloroform, n-butanol, t-butanol, or pyridine may be used to promote interaction of the compound and phospholipid. The specific procedure can be tailored to accommodate the individual properties of specific compounds.

Method II may be used to incorporate biologically active compounds or medications without regard to their solubility characteristics. In this procedure the compound is covalently attached to a lipid with the result that the lipid moiety will associate with the liposome and anchor the compound to the liposomal biolayers. Phosphatidylethanolamine and palmitic acid have been utilized for this purpose but a variety of lipids may be applicable to this method. In this procedure the compound and a lipid derivative capable of derivatizing the compound, for example, the N-hydroxy-succinimide ester of palmitic acid, N-succinyl-phosphatidylethanolamine, or alternatively phosphatidylethanolamine in the presenoe of a dehydrating agent such as N-N,-dicyclohexylcarbodiimide, are mixed in a suitable solvent and allowed to react. The lipid derivative of the compound is then purified and incorporated into liposomes. For example, egg lecithin or similar phospholipid and appropriate quantities of lipid derivatized compound are dissolved in an organic solvent and added to a suitable flask or bottle. The solution is frozen and the solvent removed in a freeze-dry apparatus. Liposomes are then formed by addition of suitable aqueous medium to the dry powder, followed by vigorous shaking of the container. It is recognized that wide variety of chemical reactions can be utilized to prepare lipid derivatives of biologically active compounds and that alternative procedures will be suitable, if the resulting derivative can be interacted with liposomes and if the biological activity of the compound has not been irreversibly destroyed by the process. It is also recognized that lipid derivatives of some compounds, for example peptides, proteins or hormones may be efficiently incorporated when added in the aqueous medium rather than to the organic solvent.

Interacted Liposome-Drug Combination

Example 1

One aspect of the invention, and the present example is directed to liposome-drug combinations where the drug is enviroxime and made according to Method I.

Figure 1A:
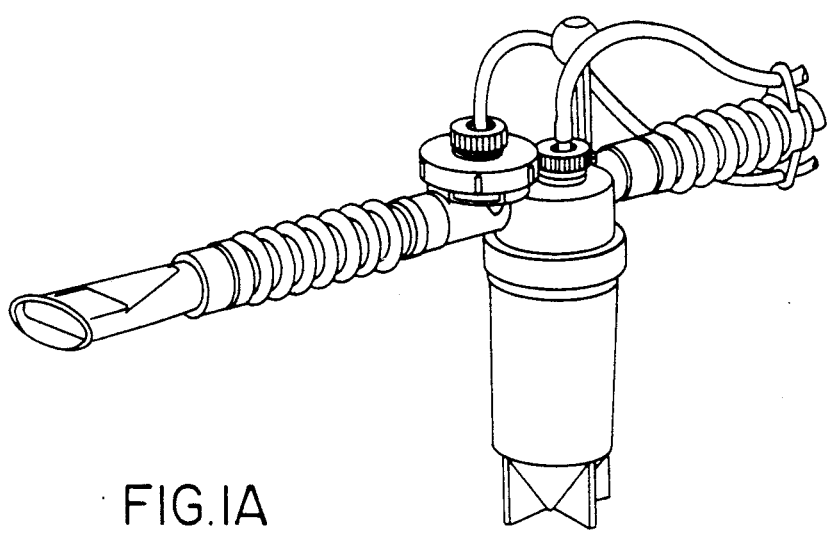

For enviroxime containing liposomes, phosphatidylcholine (450 mg) was added to a 500 mL flask in chloroform (30 mL) and 120 mg of enviroxime was added to the solution. The solvent was removed under vacuum and the lipid-drug mixture dissolved in 60 mL of T-butanol. The solution was frozen and the solvent removed in a commercial freeze-dry apparatus. Liposomes were prepared by mechanically shaking the dried residue in 30 mL of sterile water. Liposomes prepared by this procedure were examined microscopically and they were found to be heterogeneous in size ranging from less than 1 micron up to 10 microns in diameter. The preparation was then placed in a small particle aqueous aerosol generator that used a Collison nebulizer propelled by air or oxygen-enriched air for formation of the small aqueous particles. During passage through the nebulizer, the liposomes were reduced in size so that most liposomes were less than 1 micron in diameter and many less than 0.1 microns in diameter. The size of the aqueous aerosol particles containing enviroxime-liposomes delivered to the patient is controlled by the operational characteristics of the aerosol generator. The majority of these aerosol droplets were less than 5 microns in diameter with an aerodynamic mass median diameter ranging from about 1 to 3 microns. Any type of aerosol nebulizer can be used which so reduces the size of the liposomes and produces an aqueous aerosol in which the continuous phase is air or oxygen-enriched air, a number of which are available on the market. For example, the Puritan nebulizer of FIGS. 1 and 1A can be used by placing the liposomes or liposome-drug combinations in the reservoirs of these nebulizers. Accordingly, no further description of the nebulizers is deemed necessary or given.

Figure 2:
FIG. 2 is an enlargement of the liposomes in the aerosol reservoir at the start of operation of the aerosol generator.
Figure 3:
FIG. 3 is a view the same as FIG. 2 but at 60 minutes of operation. The liquid in the reservoir circulates through the nebulizer at the rate of about 60 mL per minute or 3600 mL per hour. Thus, the small volume of liquid suspension of enviroxime in liposomes is recirculated many times per hour and the liposome particles will be reduced to sub-micron diameters.
Figure 4:
FIG. 4 is a view (small enlargement) of an aerosol sample collected in an All Glass Impinger (AGI) after 15 minutes of operation. Note the small size of the particles in FIGS. 3 and 4, smaller in diameter than those in FIG. 2, at the beginning of the operation of the nebulizer.
Figure 5:
FIG. 5 is an enlarged view of the sample of FIG. 4 showing that the generation of small particle sizes has not changed the structure of the liposomes.

FIG. 2 is a photograph of enviroxime-containing liposomes as they were initially made and showing that they are very heterogeneous in size, ranging from 0.7 microns down to less than 0.03 microns in diameter. Following processing by the small particle aerosol generator (SPAG), the liposomes become more homogeneous in size, as shown in FIGS. 3 and 4, with larger ones being less than 0.35 microns in diameter. FIG. 5 is an enlargement of the liposomes of FIGS. 3 and 4 illustrating that they retain their liposomes characteristics and are multi-lamellar liposomes of "classical" structure after generation in a small particle aqueous aerosol.

Enviroxime is a substituted imidazole with exceptional potency against all rhinoviruses tested: inhibitory concentrations generally range from 0.01 to 0.120 $\mu g/mL$. Maximum tolerated concentrations for cells in culture range from 4 to 100 $\mu g/mL$, resulting in therapeutic ratios ranging from 50 to 100. Enviroxime is active also against polioviruses, echoviruses and coxsackieviruses. The drug was discovered by Eli Lilly and Company.

Enviroxime is only slightly soluble in water (1–2 $\mu g/mL$) and this has posed a problem in medical use of the drug. This difficulty is overcome by preparing liposomes of enviroxime (1–8 mg/mL) and phosphatidylcholine (15 mg/mL) in particles small enough to be administered as a small particle aqueous aerosol. By this methodology, doses of 6 to 12 mg/hr can be given to the respiratory tract.

Treatment periods of one hour to four hours per day are satisfactory. Daily dosage is set forth in Table 3 for an average-sized adult (70 kg):

TABLE 3

| Duration | Mg/Hr | Total Dose (mg) | Mg/Kg/Day |
| --- | --- | --- | --- |
| 1 hr | 6 | 6 | 0.08 |
| 1 hr | 12 | 12 | 0.16 |
| 2 hr | 6 | 12 | 0.16 |
| 2 hr | 12 | 24 | 0.32 |
| 4 hr | 6 | 24 | 0.32 |
| 4 hr | 12 | 48 | 0.64 |

Table 3 reveals that all proposed doses are substantially less than 1 mg/kg/day. Tolerance studies in animals summarized below show laok of untoward effeots with doses many-fold larger than those proposed above.

Animal Tolerance Studies: Pharmacukinetics

Effects in vitro on muscle. Muscle from many organs of rats was tested with $10^{-5}$ to $10^{-8}$M enviroxime. It did not activate adrenergic, histamine, prostaglandin E2 and a number of other biologic receptors. There was some non-competitive antagonism of dose response curves similar to that of potassium chloride.

Effects on electrolytes. At dose of 25 mg/kg and above there was significant oliguria in rats. The oliguria was associated with increases in potassium in serum but not sodium.

Effects in mice. Doses of 50 mg/kg orally produced no detectable effects. At higher doses, 100-400 mg/kg, there was increasing leg weakness, decreased motor activity and gait disturbances. The effect of high doses was rapid, occurring within a few minutes. A number of other tests were performed with oral doses and in general doses up to 100 mg/kg were well tolerated. Of particular interest was the finding that there was no immune suppressive activity of enviroxime on primary antibody response in mice.

Effects on cats and dogs. There was no significant cardiovascular effects on cats. There was some stepwise depression of diastolic blood pressure in dogs following 1, 3, and 10 mg/kg I.V. doses. Plasma concentrations of enviroxime were 3.0, 8.9 and 19 μg/mL followinq these I.V. doses. Bioassay (antiviral) and biochemical assay of blood yielded similar results.

The above studies, and others, are acceptable as evidence of adequate safety for human use and human studies.

Example 2

A further example of liposome aerosol treatment is the administration of cyclosporine A combined in liposomes of phosphatidylcholine or of phosphatidylcholine-cholesterol mixtures which are made by Method I.

For liposomes of cyclosporine A and phosphatidylcholine, phosphatidylcholine (450 mg) in 22.5 mL of chloroform was added to a 500 mL round bottom flask and 60 mg of lyophilized oyolosporine A was added. The solvent was removed under vacuum and the dried lipid-drug mixture dissolved in 60 mL of T-butanol. The solvent was again removed under vacuum and the dried residue mechanically resuspended by shaking in 30 mL of sterile phosphate buffered saline. Formation of liposomes was confirmed for ratios of cyclosporine A to phosphatidylcholine of 1:48 up to 1:12 by specific entrapment of markers. In other experiments, it was established using radiolabeled cyclosporine A that more than 83% of the drug was incorporated into the liposomes under these conditions.

Liposomes were also prepared by this procedure containing cholesterol in addition to cyclosporine A and phosphatidylcholine (Table 4). Addition of cholesterol increased the quantities of cyclosporine A that could be incorporated into liposomes by two-fold. The ratios of cyclosporine A to phosphatidylcholine found to form liposomes were 1:48 up to 1:7. Cholesterol was present at one-half the phosphatidylcholine concentration. Again, incorporation of cyclosporine A into liposomes confirmed over the range of drug concentrations and formation of liposomal permeability barriers was documented by marker entrapment.

TABLE 4

| Characterization of liposomes containing cyclosporine A | | | | | |
| --- | --- | --- | --- | --- | --- |
| Chol (mg) | EYPC (mg) | CsA (mg) | Molar Ratio CsA:EYPC | Volume Entrapped (%) | Percent Associated |
| | 7.5 | 0.25 | 1:48 | 2.2 | 77.1 |
| | 7.5 | 0.50 | 1:24 | 2.2 | 89.6 |
| | 7.5 | 1.0 | 1:12 | 2.1 | 94.7 |
| | 7.5 | 2.0 | 1:6 | 1.3 | 90.6 |
| | 7.5 | 4.0 | 1:3 | 0 | 87.3 |
| | 7.5 | 8.0 | 1:1.5 | 0 | 83.2 |
| 3.75 | 7.5 | 1.8 | 1:7 | 2.1 | 82.8 |
| 3.75 | 7.5 | 3.75 | 1:4 | 1.3 | 76.1 |

Abbreviations:
Chol, cholesterol; EYPC, egg yolk phosphatidylcholine; CsA, cyclosporine A.

Liposomes containing 2-4 mg of cyclosporine A prepared by the above procedures were also placed in a Collison small particle aerosol generator and delivery of drug containing liposomes was confirmed in particles ranging from less than 1 micron to greater than 5 microns. The aerodynamic mass median diameter of the aqueous particles in the aerosol was found to be 1.8 to 2.0 microns. This particle size range is similar as observed with other liposome preparations (e.g., enviroxime) and solutions of water soluble drugs (e.g., ribavirin).

Example 3

In this aspect of the invention and example, methotrexate is the drug in the liposome-drug combination made by Method II. (Hashimoto, K., Loader, J. E., and Kinsky, S. C., 1985, Synthesis and Characterization of Methotrexatedimyristoylphosphatidylethanolamine Derivatives and the Glycerophosphorylethanolamine Analogs. Biochim. Biophys. Acta 816:163-168; Hashimoto, K., Loader, J. E., Knight, M. S., and Kinsky, S. C., 1985, Inhibition of Cell Proliferation and Dihydrofolate Reductase by Liposomes Containing Methotrexatedimyristoylphosphatidylethanolamine Derivatives and by the Glycerophosphorylethanolamine Analogs. Biochim. Biophys. Acta 816:169-178).

Methotrexate (40 μmol) is dissolved in 0.8 mL of a 1:1 volume mixture of chloroform and methanol (hereafter abbreviated C/M) containing triethylamine (240 μmol). The following were then added sequentially to this solution while stirring: dimyristoyl-phosphatidylethanolamine (120 μmol) dissolved in 5.6 mL of C/M; N-hydroxysuccinimide (200 μmol) dissolved in 0.8 mL of C/M; N,N'-dicyclohexylcarbodiimide (200 μmol) dissolved in 0.8 mL of C/M. After incubation for 3 hours at room temperature, the reaction mixture was taken to dryness by rotary evaporation under reduced pressure at 40° C., and the residue was redissolved in 2 mL of C/M.

Chromatographic separation of the methotrexate phosphatidylethanolamine derivatives was accomplished by streaking 250 μL of this fraction on each of 8 analytical thinlayer plates (Silica gel 60 F-254, 0.25 mm, Brinkmann Instruments, Inc., Westbury, N.Y.). The plates were developed in a solvent system of chloroform/methanol/water (65:30:5 by vol.). After development, four yellow bands (I-IV) were visible that also gave a positive test for phosphate when sprayed with an acid molybdate reagent (Applied Science, Deerfield, Ill.). These bands had approximate $R_F$ values of 0.18 (I), 0.28 (II), 0.39 (III), and 0.49 (IV), whereas the $R_F$ for the unreacted methotrexate band, which did not stain for phosphate was 0.06. Band I which was shown to possess full biologic activity was scraped from the plates and suspended in 5 mL of methanol. After centrifugation (750×g for 10 min. at 4° C.), the yellow supernatant was recovered, and the pelleted silica gel particles were reextracted with another 5 mL of methanol. Ten mL of chloroform was added to the combined supernatants, and this solution was layered over a 50 mm high bed of Unisil (Clarkson Chemical Co., Williamsport, Pa.) at the bottom of a 1×20 cm column. The Unisil previously had been washed extensively with chloroform, followed by C/M. The yellow compound (designated MTXA-CMPE) was subsequently eluted by passage of 20 mL of C/M. The eluate was taken to dryness, and the residue was redissolved in 5 mL of C/M and stored at −20° C.

Liposomes were generated from dried lipid films containing dioleoyl-phosphatidylcholine (DOPC), cholesterol, and dicetylphosphate in a molar ratio of 2:1.5:0.2, respectively. The film was also supplemented with 2.5 mol% of MTX-DMPE I on the basis of phosphate content. The lipid films were dispersed by vortexing in sufficient balanced salt solution to give a 10 mM liposomal (DOPC) suspension. MTX-DMPE I had a phosphate methotrexate ratio of 1. Accordingly, the final methotrexate density in liposomes prepared with the derivative was 2.5 mol% methotrexate.

Example 4

Additional Examples of Derivatizing Lipid Insoluble Compounds for Insertion into Liposomes for Aerosolization 1. Compound: Cytosine Arabinoside
Derivative: N-Palmitoyl-1-B-D-arabinofuranosylcytosine
Class: Antiviral Liposomes were made by detergent dialysis and consisted of phosphatidylcholine, stearylamine and cholesterol (60:20:20).

Reference for synthesis: Akiyama, M., Ohishi, J. I., Shirai, T., Akashi, K., Yoshio, K. I., Nishikido, J., Hayashi, H., Usubuchi, Y., Nishimura D., Itoh, H., Shibya, C., and Ishida, T. 1978. The synthesis of new derivatives of 1-B-D-arabinofuranosyl cytosine. Chem. Pharm. Bull. 26:981-984. Reference for use: Rubar, W., Supersano, A., Weder, H. G., Hartmann, H. R., Hengartner, H., Schott, H., and Schwendener, R. 1986. Treatment of murine L1210 lymphoid leukemia and melanoma B16 with lipophilic cytosine arabinoside prodrugs incorporated into unilamellar liposomes. Int. J. Cancer 37:149-154.

2. Compound Muramyl dipeptide (MDP)
Derivative: MDP-phosphatidylethanolamine
Class: Immunotherapy Multilamellar liposomes were made by the resuspension in an aqueous medium of derivatized drug dried under vacuum and consisted of palmitoyloleylphosphatidylcholine and dioleylphosphatidylserine (7:3).

Reference for synthesis: Merser, C. and Sinay, P. 1975.

Total synthesis and adjuvant activity of bacterial peptidoglycan derivatives. Biochem. Biophys. Res. Comm. 66:1316-1322.

Reference for use: Fidler, J., Fogler, W. E., Brownhill, A. F., and Shumann, G. 1987. Systemic activation of tumoricidal properties in mouse macrophages and inhibition of melanoma metastases by the oral administration of MDP-PE, a lipophilic muramyl dipeptide. J. Immunol. 138:6509-6514.

3. Compound: Tromantadine
Derivative: Dielaidoylphosphatidylethanolaminetromantadine; Palmitoyloleylphosphatidylethanolaminetromantadine
Class: Antiviral Multilamellar liposomes were made by the resuspension in an aqueous medium of derivatized drug dried under vacuum.

Reference for synthesis: Rosenthal, K. S., Sokol, M. S., Ingram, R. L., Subramanian, R., and Fort, R. C. 1982.

Tromantadine: inhibitor of early and late events in herpes simplex virus replication. Antimicrob. Agents Chemother. 22:1031-1036.

Reference for use: Cheetham, J. J. and Epand, R. M. 1987. Comparison of the interaction of the antiviral chemotherapeutic agents amantadine and tromantadine with model phospholipid membranes. Bioscience Reports 7:225-230.

4. Compound: Hexasaccharides
Derivative: Stearylamine hexasaccharide
Class: Vaccines Hexasaccharides are coupled to the lipophilic stearylamine by the reductive amination method with sodium cyanoborohydride. Oligosaccharide-lipid conjugates are purified by Sephadex LH-20 column chromatography.

Reference for synthesis: Wood, C., and Kabat, E. A. 1981. Immunochemical studies of conjugates of isomaltosyl oligosaccharides to lipid. I. Antigenicity of the glycolipids and the production of specific antibodies to rabbits J. Exp. Med. 154:432-449.

Reference for use: Snippe, H., Zigterman, J. W. J., van Dam, J. E. G., and Kamerling, J. P. 1988. Oligosaccharidehaptenated liposomes used as a vaccine to Streptococcus pneumoniae, p. 183-196. In Gregoriadis, G. ed. Liposomes as drug carriers. John Wiley & Sons, Ltd., New York.

Example 5

Further examples numbered 4 to 14 are shown in Table 5 in which the preferred methodology for preparation in liposomes, concentration of drug in the aerosol reservoir and the amount of drug deliverd in an aqueous erosol by air or oxygen-enriched air in a specified period of time are shown. The delivered doses approximate single doses of drug which might be given by oral or parenteral routes of administration.

TABLE 5

Suggested Delivered Dose of Representative Liposome Containing Compounds as Contained in Small Particle Aqueous Aerosol Delivered by Air or Oxygen Enriched Air

| Example No. | Compound | Method[1] | Concentration in Reservoir (mg/mL) | Duration of Treatment | Estimated Delivered Dose[2] (mg) |
|---|---|---|---|---|---|
| 4 | Amantadine | 1 | 4 | 12 hrs | 172 |
| 5 | Digtoxin | 1 | 1 | 20 min | 1 |
| 6 | Isosorbide | 1 | 0.5 | 3 hrs | 5 |
| 7 | Estrogens | 1 | 0.8 | 8 hrs | 23 |
| 8 | Diabinese | 1 | 6 | 10 hrs | 216 |
| 9 | Amphotericin B | 1 | 20 | 30 min | 36 |
| 10 | Prednisone | 1 | 8 | 60 min | 29 |
| 11 | Chlorpromazine | 1 | 60 | 20 min | 72 |
| 12 | Morphine sulfate | 1 | 10 | 20 min | 12 |
| 13 | Acyclovir | 2 | 20 | 12 hrs | 864 |
| 14 | Influenza vaccine | 1,2 | 40 ug HA/mL | 20 min | 48 ug HA |

[1]Methods:
(1) As per Method I for lipophilic compounds.
(2) As per Method II for covalent attachment of compounds to the surface of the lipid bilayer.
[2]Estimated dose based on a 70% efficiency of aerosol deposition and a 10 L minute volume for a 70 kg adult, and on currently given dosages.

Also, combinations of more than one drug can be combined with small particle liposome aerosols.

Estimation of dosage of liposome-interacted drugs administered in small particle aerosol The dosage of liposome drug preparations in small particle aerosol administered by inhalation can be controlled at three different points. The first is the concentration of drug in the liposome. This is controlled by the chemical nature of the drug and the lipid of the liposome. Certain ratios of drug-liposome combinations are required to form optimally functioning liposomes. Ratios of such combinations commonly found suitable are 10% to 40% content of drug in the liposome preparation.

A second point at which regulation of dose can be achieved is the concentration of liposome-drug preparation that is added to the aqueous vehicle in the reservoir of the aerosol generator. This may range from 10 to 40 mg/mL of liposome-drug preparation in the liquid reservoir of the aerosol generator.

A third method of regulation of dose is the duration of treatment. This is usually measured in hours or fractions of hours as illustrated below. By using the three methods above a wide-range of dosage of liposome-drug preparations to the respiratory tract may be achieved. Thus, a general formulation can be derived: Total drug administered ≈ Concentration of the drug in the liposome × Concentration of liposome in aerosol generator × Duration of treatment.

Figure 6A:
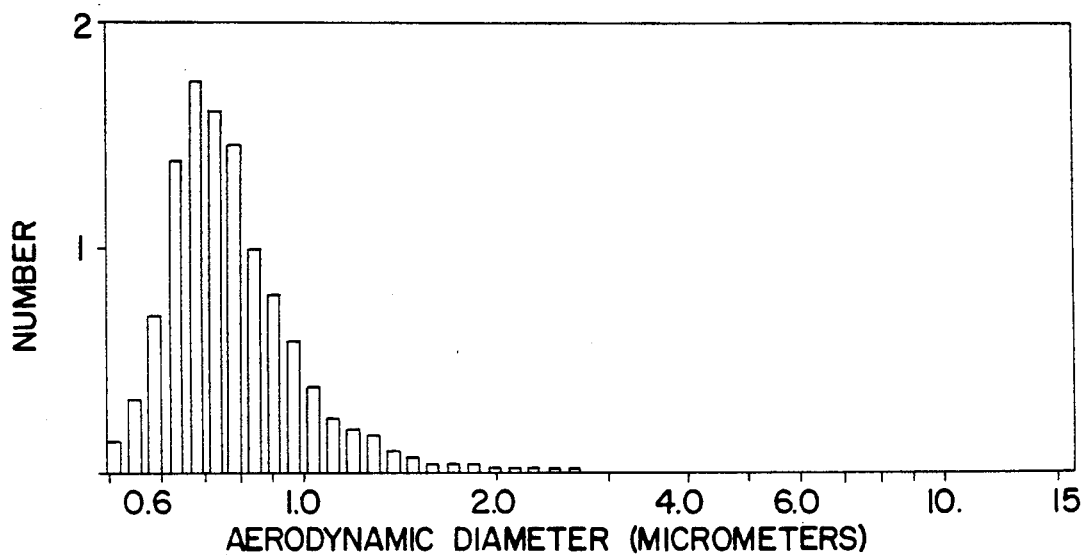
FIGS. 6A and 6B are graphs of aerodynamic particle size of enviroxime-liposome aerosol by TSI particle size instruments.
Figure 6B:
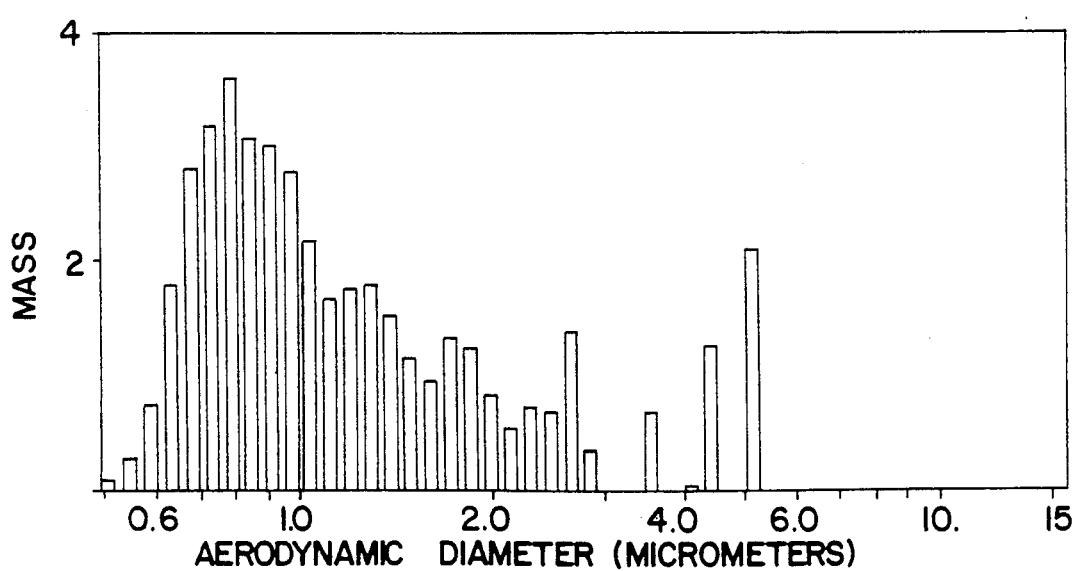

Retention by patients of drugs following inhalation in small particle aerosol can be estimated. The basis for estimates includes particle size distribution, density of particles, concentration of drug in particles, age, sex, and other factors (Knight, V., Yu, C. P., Gilbert, B. E., and Divine, G. W. 1988, Estimating the dosage of Ribavirin Aerosol According to Age and Other Variables. Journal Infect. Dis. 158(2):443–448). Liposome-drug aerosols suspended in watery media are aqueous aerosols and their particle size distribution corresponds closely with aqueous aerosols. This is demonstrated in FIGS. 6A and 6B where the particle size distribution of a liposome-enviroxime aerosol was measured from a Collison generator (SPAG-2-6000 model). The liposome-enviroxime preparation consisted of 450 mg of egg yolk lecithin and 120 mg of enviroxime combined in liposomes. This material was suspended in 30 mL of distilled water for use. Thus, the enviroxime concentration was 4 mg/mL. The APS 3300 particle size analyzer (TSI, Inc.) was used to count particles. The sample time was 20 seconds and assumed density of aerosol particles was 1.0 g/cm$^3$. The nebulizer pressure was 26 psi and the flow rate was 7.5 lpm. The drying air flow rate was 5.0 lpm. Thus, the total flow rate was 12.5 lpm. Four runs were made with the following AMMD particle size: 1.00, 1.15, 1.41, and 0.98 (mean 1.15 microns). The AMMD of the test shown was 1.00 microns. It was found that the aerodynamic mass median diameter (AMMD) approximated 1.0 micron and virtually all particles were less than 5 microns in diameter. This value is similar to that of small particle aqueous aerosols produced by this generator when there are no liposomes present. This measurement was representative of four tests. Because of this close similarity, it is reasonable to use the method of estimation of respiratory tract dosage for aqueous aerosols to estimate dosage of liposome-enviroxime and other similar aerosols.

Figure 7:
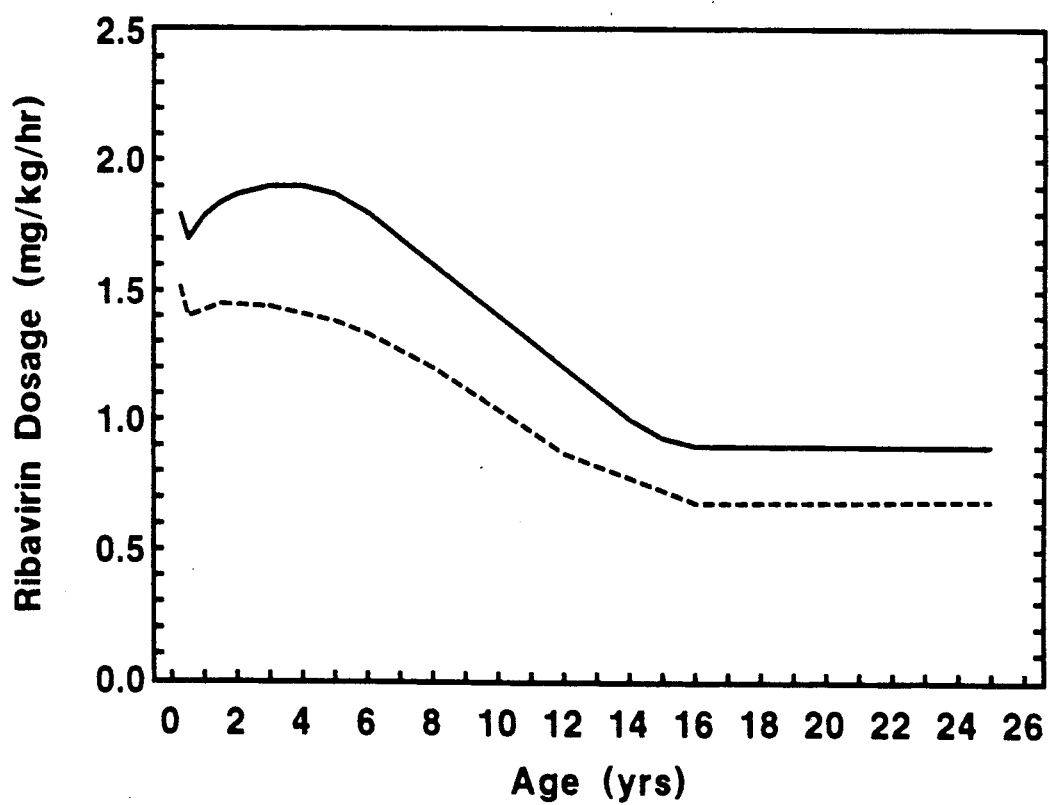
FIG. 7 is a nomogram derived to estimate aerosol dosage based on the concentration of the drug (ribavirin) in aqueous liquid in the aerosol generator.

FIG. 7 shows a nomogram which was derived to estimate aerosol dosage based on the concentration of the drug ribavirin in the aqueous liquid of the aerosol generator. By determining the ratio of the concentration of ribavirin and enviroxime in the aerosol reservoir, the estimated dosage of enviroxime administered in liposomes can be obtained. The ribavirin aerosol contains 20 mg/mL of ribavirin in the liquid reservoir at the beginning of treatment and the enviroxime concentration is 4 mg/mL. Thus, to predict the dose of enviroxime aerosol retained by the patient, the concentration of enviroxime in the reservoir liquid (4 mg/mL) is divided by the concentration of ribavirin in the reservoir liquid (20 mg/mL). The dose of enviroxime retained after inhalation of aerosol would be 20 percent of that of ribavirin retention. Thus, from FIG. 7, a dose of enviroxime for a 25 year old male would be 0.18 mg/hr (0.9 mg/kg/hr of ribavirin retained × 0.2 ratio of enviroxime concentration to ribavirin concentration) × 70 (weight of patient in Kg) or 12.6 mg retained per hour of treatment. With this methodology, it is possible to estimate the dosage of any drug contained in liposomes administered by small particle aerosol. Table 1 shows a list of drugs which are lipophilic in nature and may be prepared in liposomes and administered in small particle aerosol. The usual dosages of those drugs by other routes is indicated. In general, dosage by liposome aerosol would be appreciably less than that recommended by other routes.

Advantageously, small particle aqueous aerosol droplets containing interacted liposome-drug combination particles treatment leads to deposition of drug and liposomes throughout the respiratory tract in substantial concentrations that can treat infections that are localized to the respiratory tract. In the case of viruses, the infection is localized to respiratory epithelial cells. In the case of bacteria or fungi, the diseases will be contained in inflammatory exudates and alveoli and in other anatomical spaces in the lung and within tissues of the lung at various locations. Aerosolized interacted liposome-drug will be deposited on these sites.

In the case of lung tumors of primary or secondary origin, the tumor masses would be the site of deposition of aerosol interacted liposome-anti cancer drugs.

In the case of asthma, aqueous aerosolized liposome bronchodilator agents would be deposited throughout the bronchial tree at sustained levels for extended periods of time to provide optimum therapeutic effect.

In the case of psychiatrically useful drugs, hormones, or cardioactive agents, systemic absorption following aqueous aerosol interacted liposome-drug administration would occur at an even rate without high peaks in plasma concentration thus avoiding potential toxicity and prolonging therapeutic effect.

Aqueous aerosol droplets containing liposomes alone may replace natural surfactants in the lung of victims of drowning, chemical inhalational poisoning, and in premature infants deficient in surfactant.

Influenza or other vaccines can be given conveniently in small particle aqueous aerosol liposomes deposited by air or oxygen-enriched air directly on immunoreactive cells in the lung to elicit locally protecting immune responses. Humoral antibody may also be so stimulated.

Incorporation of some toxic agents such as amphotericin B into liposomes in aqueous aerosolized form retards their absorption into cells of the respiratory tract and reduces the toxic effect of the toxic agents without reducing their therapeutic effect.

Also, incorporation of polypeptides, oligonucleotides, enzymes, or other compounds which might be destroyed or inactivated by localized enzymes may be protected from this effect when incorporated in small particle aqueous aerosolized particles containing liposomes thus increasing their therapeutic effect.

Thus, while specific examples of a variety of small particle aqueous aerosol droplets containing liposome particles and interacted liposome-drug combination particles have been given for purposes of disclosure, the present invention is applicable to all drugs or medications and combinations of them interacted with liposomes which can be incorporated in such small particle aqueous aerosol droplets for a wide variety of disease. Also, as previously mentioned, the dosage of these liposome-drug combinations vary widely depending on the drug, duration of treatment and the like.

Accordingly, the present invention is well suited and adapted to attain the ends and carry out the objects and has the advantages and features set forth as well as others inherent therein. While presently preferred embodiments, uses, and treatments of various disease have been given for the purpose of disclosure, changes therein, modifications thereto, and other uses and treatments of disease can be made which are within the spirit and scope of the invention as defined by the following claims.

What is claimed is:

1. Aqueous aerosol droplets containing one or more liposome particles, the majority of the mass of the aerosol droplets having a diameter from 1 to 5 microns, and having an aerodynamic mass median diameter ranging from about 1 to 3 microns, the liposome particles being substantially homogeneous in size and having a diameter of less than 1 micron thereby providing deposition of the droplets containing the one or more liposome particles throughout a respiratory tract of a patient when inhaled.

2. Aqueous aerosol droplets containing one or more liposome particles and one or more lipophilic medications interacted with the liposome's membrane, the majority of the mass of the aerosol droplets having a diameter from 1 to 5 microns, and having an aerodynamic mass median diameter ranging from about 1 to about 3 microns, the particles being substantially homogenous in size and having a diameter of less than 1 micron thereby providing deposition of the droplets containing the one or more liposome particles through out a respiratory tract of a patient when inhaled.

3. Aqueous aerosol droplets containing one or more liposome particles having multiple aqueous compartments and one or more lipophilic medications interacted with membranes of the liposome particles, the majority of the mass of the aerosol droplets having a diameter of from 1 to 5 microns, and having an aerodynamic mass median diameter ranging from about 1 to about 3 microns, the particles being substantially homogeneous in size and having a diameter of less than 1 micron thereby providing deposition of the droplets containing the one or more liposome particles throughout a respiratory tract of a patient when inhaled.

4. The aqueous aerosol droplets of claim 2 wherein, the medication is selected from a lipophilic or a compound made lipophilic by derivatization of the group consisting of antiasthma, antiarrhythmic, antifungals, antihypertensive, anticancer, antibiotics, antidiabetics, antihistamines, antiparasitics, antivirals, cardiac glycosides, hormones, immunotherapies, antihypotensives, steroids, sedatives and analgesics, tranquilizers, vaccines, and cell surface receptor blockers.

5. The aqueous aerosol droplets of claim 3 where, the one or more medications are selected for man insoluble or a compound made lipophilic by derivatization of the group consisting of antiasthma, antiarrhythmic, antifungals, antihypertensives, anticancer, antibiotics, antidiabetics, antihistamines, antiparasitics, antivirals, cardiac glycosides, hormones, imunotherapies, antihypotensives, steroids, sedatives, and analgesics, tranquilizers, vaccines, and cell surface receptor blockers.

6. A method of treating a patient comprising, introducing into the respiratory tract of the patient the aqueous aerosol droplets of claim 1 by one of air and oxygen enriched air.

7. A method of treating a ptient comprising, introducing into the respiratory tract of the patient the aqueous aerosol droplets of claim 2 by one of air and oxygen enriched air.

8. A method of treating a patient comprising, introducing into the respiratory tract of the patient the aqueous aerosol droplets of claim 3 by one of air and oxygen enriched air.

9. A method of treating a patient comprising, introducing into the respiratory tract of the patient the aqueous aerosol droplets of claim 4 by one of air and oxygen enriched air.

10. A method of treating a patient comprising, introducing into the respiratory tract of the patient the aqueous aerosol droplets of claim 5 by one of air and oxygen enriched air.

11. A method of generating the aqueous aerosol droplets of claim 1 comprising, nebulizing heterogeneous particles of liposomes in an aqueous medium with air or oxygen enriched air by a nebulizer effective to produce the aqueous aerosol droplets and homogenize the particles of liposomes.

12. A method of generating the aqueous aerosol droplets of claim 2 comprising, nebulizing the particles of liposomes and the one or more medications with the liposome's membrane of heterogeneous size in an aqeuous medium with air or oxygen enriched air in a nebulizer effective to produce the aerosol droplets and to homogenize the particles without loss of the medications and their activity.

13. A method of generating the aqueous aerosol droplets of claim 3 comprising, nebulizing the particles of liposomes and the one or more lipophilic medications interacted with the membranes of the liposomes of heterogeneous size in an aqueous medium with air or oxygen enriched air in a nebulizer effective to produce the aerosol droplets and to homogenize the particles of liposomes without loss of medication and its activity.

14. A method of generating the aqueous aerosol droplets of claim 4 comprising, nebulizing the particles of liposomes and the selected medication of heterogeneous size in an aqueous medium with air or oxygen enriched air in a nebulizer effective to produce the aerosol droplets and to homogenize the particles of liposomes without loss of the medication and its activity.

15. A method of generating the aqueous aerosol droplets of claim 5 comprising, nebulizing the liposome particles and the selected medication of heterogeneous size in an aqueous medium with air or oxygen enriched air in an nebulizer effective to produce the aerosol droplets and to homogenize the liposome particles without loss of the medication and its activity.

16. An aerosol container having a reservoir containing the liposome particles of claim 1 in n aqueous medium, and having aerosol generating means including an air or an oxygen enriched air source in fluid communication with the reservoir effective to produce the aqueous aerosol droplets.

17. An aerosol container having a reservoir containing the liposomes and medications of claim 2 in an aqueous medium, and having aerosol generating means including an air or oxygen enriched air source in fluid communication with the reservoir effective to produce the aqueous aerosol droplets.

18. An aerosol container having a reservoir containing the liposomes and medications of claim 3 in an aqueous medium, and having aerosol generating means including an air or oxygen enriched air source in fluid communication with the reservoir effective to produce the aqueous aerosol droplets.

19. An aerosol container having a reservoir containing the liposomes and medications of claim 4 in an aqueous medium, and having aerosol generating means including an air or oxygen enriched air source in fluid communication with the reservoir effective to produce the aqueous aerosol droplets.

20. An aerosol container having a reservoir containing the liposomes and medications of claim 5 in an aqueous medium, and having aerosol generating means including an air or oxygen enriched air source in fluid communication with the reservoir effective to produce the aqueous aerosol droplets.

21. A method of producing the aerosol droplets of claim 1 comprising, placing heterogeneous particles of the liposomes in an aqueous medium in an aerosol reservoir, and aerosolizing the heterogeneous particles of liposomes with air or oxygen enriched air effective to produce the aqueous aerosol droplets and to homogenize the heterogeneous particles of liposomes.

22. A method of producing the aerosol droplets of claim 2 comprising, placing heterogeneous particles of the liposomes and medication in an aqueous medium in an aerosol reservoir and aerosolizing the heterogeneous particles of liposomes and medication with air or oxygen enriched air effective to produce the aqueous aerosol droplets and to homogenize the heterogeneous particles of liposomes.

23. A method of producing the aerosol droplets of claim 3 comprising, placing the particles of medications interacted with membranes of the liposomes of heterogeneous size in an aqueous medium in an aerosol reservoir, and aerosolizing them with air or oxygen enriched air effective to produce the aerosol droplets and to homogenize the heterogeneous particles.

24. A method of producing the aerosol droplets of claim 4 comprising, placing the particles of medication interacted with membranes of liposomes of heterogeneous size in an aqueous medium in an aerosol reservoir, and aerosolizing them with air or oxygen enriched air effective to produce the aerosol droplets and to homogenize the heterogeneous particles.

25. A method of producing the aerosol droplets of claim 5 comprising, placing the particles of one or more medications interacted with membranes of the liposomes of heterogeneous size in an aqueous medium in an aerosol reservoir, and aerosolizing them with air or oxygen enriched air effective to produce the aerosol droplets and to homogenize the heterogeneous particles.

* * * * *

UNITED STATES PATENT AND TRADEMARK OFFICE
CERTIFICATE OF CORRECTION

PATENT NO. : 5,049,388

DATED : September 17, 1991

INVENTOR(S) : Jack V. Knight, et al

It is certified that error appears in the above-identified patent and that said Letters Patent is hereby corrected as shown below:

Column 3, line 54, "Advantageously" should read -- Advantageously --.

Column 3, line 54, "partiole" should read -- particle --.

Column 3, line 56, "homoqenized" should read -- homogenized --.

Column 4, line 39, "oxygen- C enriched" should read -- oxygen-enriched --.

Column 6, line 33, "hydrophobic ionic," should read -- hydrophobic, ionic, --.

Column 6, line 40 "liposome" should read -- liposomes --.

Column 7, line 47, "solbule" should read -- soluble --.

Column 11, line 19, "laok" should read -- lack --.

Column 11, line 19, "effeots" should read --effects--.

Column 11, line 62, "oyolosporine" should read -- cyclosporine --.

Column 13, line 7, "thinlayer" should read -- thin layer --.

Column 14, line 3, "Compound" should read -- Compound: --.

Claim 4, Column 18, line 37, "wherein," should read -- where --.

UNITED STATES PATENT AND TRADEMARK OFFICE
CERTIFICATE OF CORRECTION

PATENT NO. : 5,049,388

DATED : September 17, 1991

INVENTOR(S) : Jack V. Knight, et al

It is certified that error appears in the above-identified patent and that said Letters Patent is hereby corrected as shown below:

Claim 4, Column 18, line 41, "antihypertensive," should read --antihypertensives--.

Signed and Sealed this

Sixth Day of July, 1993

Attest:

MICHAEL K. KIRK

Attesting Officer

Acting Commissioner of Patents and Trademarks